United States Patent [19]

Gatehouse et al.

[11] Patent Number: 5,545,820

[45] Date of Patent: Aug. 13, 1996

[54] INSECT CONTROL USING LECTINS HAVING SPECIFIC MANNOSE-BINDING ABILITY

[75] Inventors: Angharad Gatehouse; Vaughan Hilder, both of Durham, United Kingdom; Els Van Damme; Willy Peumans, both of Heverlee, Belgium; Christine Newell; William Hamilton, both of Cambridge, United Kingdom

[73] Assignee: Agricultural Genetics Company Limited, Cambridge, United Kingdom

[21] Appl. No.: 425,315

[22] Filed: Apr. 17, 1995

Related U.S. Application Data

[63] Continuation of Ser. No. 969,841, Jan. 28, 1993, abandoned which is a continuation of PCT/GB91/01290, Jul. 30, 1991.

[30] Foreign Application Priority Data

Jul. 30, 1990 [GB] United Kingdom .................. 9016687
May 24, 1992 [GB] United Kingdom .................. 9111346

[51] Int. Cl.⁶ .............................. A01H 5/00; A01C 1/06; A01N 25/26; C07H 21/04; C07K 14/415; C12N 15/29

[52] U.S. Cl. ................................ 800/205; 800/DIG. 43; 435/172.3; 435/320.1; 424/418; 536/23.6; 530/370; 47/58

[58] Field of Search ................... 800/200, 205, 800/250, 255, DIG. 9, DIG. 43, DIG. 53, DIG. 59; 435/69.1, 172.1, 172.3, 320.1; 424/405, 418; 47/58.03, 58; 536/23.6; 530/370

[56] References Cited

FOREIGN PATENT DOCUMENTS 0351924 1/1990 European Pat. Off. .

OTHER PUBLICATIONS

Van Damme et al. 1987. Febs Letters. 215(1): 140–144.
Van Damme et al. 1988. Physioligia Plontarum. 73: 52–57.
Matsuda et al. 1981. Febs Letters. 126(1): 111–113.
Sambrook et al. 1989. Molecular Cloning—A Laboratory Manual. 2nd Ed. pp. 11.2–11.19, 11.45–11.49, 11.52–11.61.
Osborn et al. 1988. Science. 240: 207–210.
De Meirsman et al. 1986. Lectins. vol. V: 117–123.

Primary Examiner—Erich E. Veitenheimer
Attorney, Agent, or Firm—Lowe, Price, LeBlanc & Becker

[57] ABSTRACT

The invention relates to the use of lectins having specific mannose-binding ability and/or derived from Amaryllidaceae or Alliaceae for the control of insect pests. Transgenic plants containing and capable of expressing foreign genes coding for such lectins are also disclosed.

15 Claims, 4 Drawing Sheets

INSECT CONTROL USING LECTINS HAVING SPECIFIC MANNOSE-BINDING ABILITY

This application is a continuation of application Ser. No. 07/969,841 filed Jan. 28, 1993, now abandoned, which is a continuation of PCT/GB91/01290, filed Jul. 30, 1991.

BACKGROUND OF THE INVENTION

The present invention relates to the use of certain lectins for the control of insect pests.

Lectins are a heterogeneous class of (glyco) proteins grouped together based upon their ability to recognize and bind carbohydrate moieties of glycoconjugates. Chitin, the principal structural carbohydrate of insects, is a polymer of N-acetyl glucosamine [GluNAc] and various lectins with sugar binding specificities for GluNAc have been disclosed with insecticidal activity against certain agricultural pests.

EP-A-0351924 (Shell Internationale Research Maatschappij B.V.) relates to a transgenic plant comprising a lectin gene expressing a lectin within the plant foreign to the plant as found in nature. In particular, it discloses that pea lectin has been inserted into tobacco, and the transgenic plant has some degree of insect resistance.

EP-A-0427529 (Pioneer Hi-Bred International, Inc) discloses that selected plant lectins have been found to be larvicidal against a number of common insect pests or agricultural crops.

Many lectins are known to be toxic to mammals and birds. For example, the lectins of *Phaseolus vulgaris* are poorly digested by rats and thus are able to react with intestinal cells causing disruption of the brush borders of duodenal and jejunal enterocytes. As a result, abnormal absorption of potentially harmful substances occurs, leading to severe toxic effects (Pusztai et al, 1979).

There is a need, therefore, to identify lectins which are toxic to insects but at the same time do not exhibit toxicity to mammals or birds. These would be useful in crop protection applications without restriction on the food use of the material in which the foreign lectin is to be presented.

SUMMARY OF THE INVENTION

We have surprisingly found that a group of lectins, characterised by specific mannose-binding ability, in particular derived from Amaryllidaceae and Alliaceae, are effective for the control of insect pests, but are non-toxic to mammals and birds.

In its broadest aspect this invention relates to the use of lectins having specific mannose-binding ability and/or derived from Amaryllidaceae and Alliaceae for the control of insect pests. Specifically, such lectins are presented to insects in amounts likely to cause mortality, reduced larval weight and/or delayed development. As a result of the presentation of such lectins to insect pests of plants, plants may be protected from damage to leaves, stems, tubers, fruits and other useful parts. Such lectins are, on the other hand, non-toxic to mammals and constitute a safer alternative to the use of chemical insecticides.

The lectins used according to this invention exhibit highly specific mannose-binding properties. Although lectins from some other plants, e.g. legumes, may bind mannose, they also bind glucose and N-acetyl glucosamine. Specific mannose-binding ability is therefore the ability to bind mannose together with inability to bind glucose and N-acetyl glucosamine. Such binding specificity may be established by the techniques of quantitative precipitation, hapten inhibition and affinity chromatography as detailed in Shibuya et al., 1988.

Recent work comparing lectins from Amaryllidaceae and Alliaceae indicates that lectins from Alliaceae strongly resemble those of Amaryllidaceae with respect to their molecular structure, carbohydrate binding specificity, amino acid composition and serological properties. All bind D-mannose exclusively. All contain high amounts of acidic and hydroxylic amino acids, glycine and leucine. All contain subunits of Mr 11,500–14,000, not linked by disulphide bonds and may occur as dimers (eg. garlic) or tetramers (eg. snowdrop). Generally, lectin concentration is higher in bulbs of Amaryllidaceae than it is in bulbs of Alliaceae.

A preferred use of Amaryllidaceae and Alliaceae lectins according to the invention is to insert the genes encoding these proteins into plants. Previous applications have described the successful insertion of genes for proteins with insecticidal activity such as the Bt toxin (e.g. EP 0 142 924—Lubrizol Genetics Inc.) and trypsin inhibitors eg. from cowpea. (EP 0 272 144—Agricultural Genetics Company).

Various methods are available to those skilled in the art for the introduction and expression of foreign genes in transgenic plants. These include Agrobacterium mediated gene transfer, microinjection of DNA into cells or protoplasts, DNA transfer via growing pollen tubes, DNA uptake by imbibing zygotic embryos, silicon carbide fibre mediated delivery, microprojectile bombardment [biolistic transfer] and direct DNA uptake employing polyethylene glycol, liposomes or electroporation. Once a line of transgenic plants is established the character may be transferred to other cultivars by conventional plant breeding.

Lectins useful in insect control and the corresponding genes can be obtained from, but are not necessarily limited to, *Allium sativum* (garlic), *Allium vineale, Allium ursinum, Allium moly, Allium cepa, Allium porrum, Narcissus pseudonarcissus, Clivia miniata, Galanthus nivalis* (snowdrop) and *Hippeastrum hybr.*

Alternatively, these proteins may be administered or co-administered directly to plants using an agrochemical formulation or as part of a pesticidal formulation which may also include *Bacillus thuringiensis*, Bt toxin, trypsin inhibitors or other insecticidal substances.

Insects to be controlled include the plant-chewing stages of insects belonging to the orders Coleoptera, Lepidoptera and Orthoptera, including, but not limited to: *Acanthoscelides obtectus, Bruchus sps., Callosobruchus sps.* [bruchid beetles], *Agriotes sps.* [wireworms], *Amphimallon sps.* [chafer beetles], anthonomus grandis [cotton boll weevil], *Ceutorhynchus assimilis* [cabbage seed weevil], *Cylas sps.* (sweet potato weevils], *Diabrotica sps.* [corn rootworms], *Epicauta sps.* [black blister beetles], *Epilachna sps.* [melon beetles etc.], *Leptinotarsa decemlineata* [Colorado potato beetle], *Meligisthes sps.* [blossom beetles], *Melolontha sps.* [cockchafers], *Phyleotreta sps., Psylliodes sps.* [flea beetles], *Popillia japonica* [Japanese beetle], *Scolytus sps.* [bark beetles], *Sitophilus sps.* {grain weevils], *Tenebrio molitor* [yellow mealworm], *Tribolium sps.* [flour beetles], *Trogoderma granarium* [Khapra beetle], *Acleris sps.* [fruit tree tortrixs], *Acraea acerata* [sweet potato butterfly], *Agrotis sps.* [cutworms], *Autographa gamma* [silver-Y moth], *Chilo sps.* [stalk borers], *Cydia pomonella* [codling moth], *Diparopsis sps.* [red bollworms], *Ephestia sps.* [warehouse moths], *Heliothis sps., Helicoverpa sps.* [budworms, bollworms], *Mamestra brassicae* [cabbage moth],

*Manduca sps.* [hornworms], *Maruca testulalis* [mung moth], *Mythimna sps.* [cereal armyworms], *Ostrinia nubilalis* [European corn borer], *Pectinophora gossypiella* [pink bollworm], *Phthorimaea operculella* [potato tuber moth], *Pieris brassicae* [large white butterfly], *Pieris rapae* [small white butterfly], *Plodia interpunctella* [Indian grain moth], *Plutella xylostella* [diamond-back moth], *Sitatroga cerealella* [Angoumois grain moth], *Spodoptera sps.* [armyworms], *Trichoplusia ni* [cabbage semilooper], *Acheta sps.* [field crickets], *Gryllotalph sps.* [mole crickets], *Locusta migratoria* [migratory locust] and *Schistocerca gregaria* [desert locust].

Lectins used according to this invention are particularly effective against insect pests of the Coleoptera order.

Plants which can be protected, preferably by transformation, according to the methods of this invention include, but are not limited to: rice, wheat, maize, cotton, potato, sugarcane, grapevines, cassava, sweet potato, tobacco, soyabean, sugar beet, beans, apple, tomato, oilseed rape and sunflower.

DESCRIPTION OF THE PREFERRED EMBODIMENTS

Extraction of Lectins from Plant Material

Figure 1:
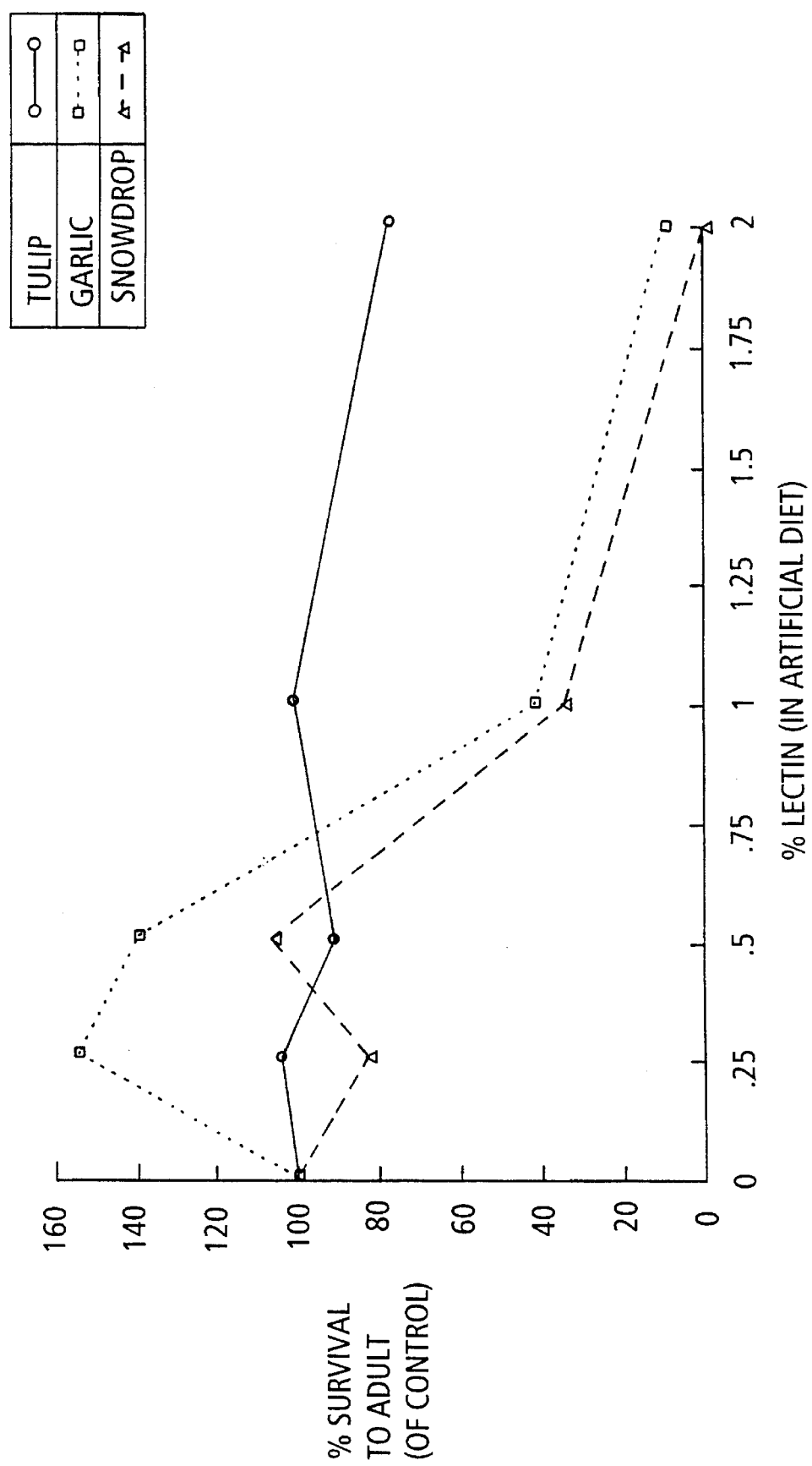
FIG. 1. Effect of lectins on survival of Bruchid Beetle following incorporation into artificial seed diet.

For the purposes of extracting lectins from Amaryllidaceae and Alliaceae species the following procedure may be followed.

The bulbs or leaves are homogenized with a blender using 50 ml of 1M ammonium sulphate per gram of fresh tissue. Afterwards the extract is filtered through cheese cloth and centrifuged (4,000 g for 10 minutes). The resulting supernatant is frozen overnight at −20° C. After thawing, the precipitate is removed by a second centrifugation. The clarified supernatant is applied to a column of mannose-Sepharose (50 ml bed volume) equilibrated with 1M ammonium sulphate. Unbound proteins are washed off and lectin is desorbed using unbuffered 20 mM 1,3-diaminopropane.

To remove all phenolic compounds, the affinity purified lectin is brought up to 1M ammonium sulphate by adding the solid salt, and applied to a column of phenyl Sepharose (Trade-mark) (15×3 cm) equilibrated with 1M ammonium sulphate. After washing the column, lectins are eluted using distilled water or 1,3-diaminopropane (20 mM, unbuffered solution).

Cloning of Lectin Genes for Insertion into Plants

The cloning of genes for Amaryllidaceae and Alliaceae lectins poses special problems. Extraction of RNA from bulb tissues is particularly difficult. It has been found that ovary tissue, where lectins have been found to be abundant, is suitable for the extraction of mRNA.

The following describes a method for obtaining lectin genes from snowdrop (*Galanthus nivalis*). Those skilled in the art would know that this protocol could be adapted easily for other members of Amaryllidaceae or Alliaceae.

Flowering plants of snowdrop are collected and the ovaries excised from the flowers, frozen in liquid nitrogen and stored at −80° C. Total cellular RNA is prepared from ovary tissue essentially as described by Finkelstein and Crouch (1986). Poly A rich RNA is purified by chromatography on oligo-deoxythymidine cellulose (Sigma Chemical Company, St. Louis) as described by Siflow et al (1979) except that poly A rich RNA is eluted at room temperature.

A cDNA library can be made using the poly A enriched RNA isolated using a cDNA synthesis kit, eg. from Pharmacia, Uppsala, Sweden, and inserted into the EcoRI site of a multifunctional phagemid $pT_7T_3l8U$ (Pharmacia, Sweden). The library is propagated in *E. coli* XL1 Blue (Stratagene, La Jolla, Calif.).

In order to select clones recombinant for the lectin gene, the colonies are screened using a 32p-end-labelled partially degenerate oligonucleotide probe derived from the amino acid sequence of the lectin for residues 41–45 i.e.:

5' TGT GTT TGT TGC CCA 3' SEQ ID NO: 1

5' TGT GTT TGT AGC CCA 3' SEQ ID NO: 2

5' TGT GTT TGT GGC CCA 3' SEQ ID NO: 3

Hybridization is carried out for 12 hours at 38° C. in 0.9M sodium chloride containing 90 mM, Tris-HC1 pH 7.5, 6 mM EDTA, 10×Denhardts, 0.1% SDS, 180 mg/ml hydrolyzed yeast RNA and $2×10^6$ cpm/ml $^{32}$P-labelled probe. After hybridization filters are washed four times in 6×SSC (1×SSC=0.9M sodium chloride and 0.09M sodium citrate, pH 7.0) at room temperature for 15 minutes followed by a 5 minute wash at hybridization temperature in 6×SSC. Filters were blotted dry, wrapped in Saran Wrap and exposed to Kodak-X-Omat film at −80° C. Colonies producing positive signals are rescreened using the same probe under the same conditions. Plasmids are isolated from purified colonies using the alkaline lysis method as described by Birnboim and Doly (1979) and sequenced to identify the lectin gene using the dideoxy method (Sanger et al, 1977).

Complete nucleotide sequences for cDNA's corresponding to several isoforms of snowdrop lectin are shown in the accompanying sequence listings. The lectin cDNA LEC-GNA2 contains an open reading frame of 570 nucleotides with a probable initiation codon at position 18. Translation starting with this codon generates a 157 amino acid polypeptide with a calculated molecular weight of 16,917 dalton that corresponds to an in vitro translation product for snowdrop lectin. The 3' untranslated region contains six in-frame termination codons and one possible polyadenylation signal at position 532. Comparison of the aminoterminal sequence for the lectin and the deduced amino acid sequence for the lectin clone shows that the lectin is synthesized with a leader (signal) sequence of 23 amino acids (2315 dalton). It is also probable that 22 amino acids (2278 dalton) are removed post translationally from the C-terminal end of the protein.

References

Etzler, M. E. (1986) Distribution and function of plant lectins. In: The Lectins: Properties, Functions and Applications in Biology and Medicine, pp 371–435, Liener, I. E., Sharon, N., Goldstein, I. J., Eds., Academic Press Inc.

Shibuya, N., Goldstein, I. J., Van Damme, E. J. M. and Peumans, W. J. (1988) Binding properties of a mannose specific lectin from snowdrop (*Galanthus nivalis*) bulb. Journal of Biological Chemistry 263 728–734.

Puztai, A., Clarke, E. M. W., King, T. P. (1979) The nutritional toxicity of *Phaseolus vulgaris* lectins. Nutritional Society 38 115–120.

Gatehouse, A. M. R., Dewey, F. M., Dove, J. D., Fenton, K. A. and Puztai, A. (1984) Effect of seed lectins from *Phaseolus vulgaris* on the development of larvae of *Callosobruchus maculatus*; mechanism of toxicity. J. Sci. Food Agric. 35 373–380.

Finkelstein, R. R. and Crouch, M. L. (1986) Rapeseed embryo development of culture on high osmoticum is similar to that in seeds. Plant Physiology 81 907–912.

Siflow, C. D., Hammett, J. R., Key, J. L. (1979) Sequence complexity of polyadenylated ribonucleic acid from soybean suspension culture cells. Biochemistry 18 2725–2731.

Birnboim, H. C. and Doly, J. (1979) A rapid alkaline extraction procedure for screening recombinant plasmid DNA. Nucleic Acids Research 7 1513–1522.

Sanger, F., Nicklen, S. and Coulson, A. R. (1977) DNA sequencing with chain determining inhibitors. Proc. Natl. Acad. Sci 74 5463–5467.

The Effect of Lectins on Insect Pests

In order to test for the insecticidal properties of lectins from Amaryllidaceae or Alliaceae they may be incorporated into various artificial diets, applied to the surface of leaves or the genes used to transform plants to produce the proteins.

EXAMPLE 1

Lectins purified from snowdrop and garlic were incorporated into artificial seed diet (comprising chickpea meal in a cling-film skin) and tested on the bruchid beetle *Callosobruchus maculatus*.

The effect on survival of the insect larvae at various concentrations of lectin incorporation (versus controls) is shown in FIG. 1. At lower levels the garlic lectin increased survival of the bruchid beetles, but this effect was completely reversed at levels above 1% of diet and was not observed for the snowdrop lectin. The results indicate an LCs0 for the garlic and snowdrop lectins of around 0.9%. Another lectin from tulip (in a closely related family—Liliaceae) showed no insecticidal activity.

EXAMPLE 2

One of the difficulties in bioassaying the activity of such lectins is that in some artificial diets the lectin binds to mannose in the diet and becomes unavailable to the consuming insect. To overcome this problem and to analyze the effect of lectin obtained from snowdrop against *Spodoptera littoralis* (armyworm) a special artificial diet consisting of communion wafers was devised, whereby 5% snowdrop lectin (w/w) was applied to communion wafers in a solution of water. Spodoptera were fed on the wafers, which were replaced every two days.

Figure 2:
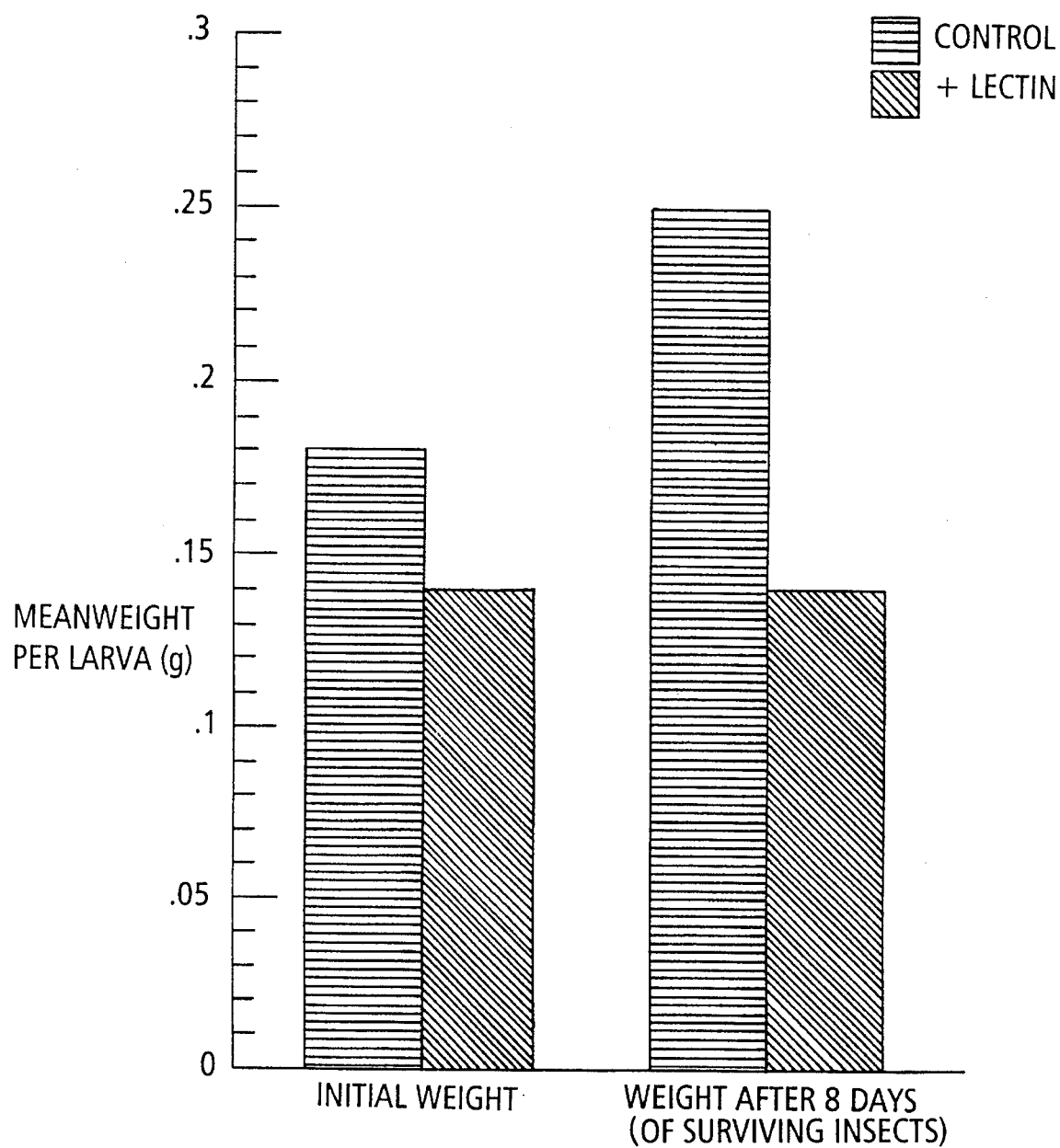
FIG. 2. Effect of Snowdrop Lectin on larval development of *Spodoptera littoralis*.

FIG. 2 and Table 1 show the effect on survival and weight gain of surviving insects. The results show that 5% snowdrop lectin reduces the survival of Spodoptera larvae and substantially reduces the weight gain of surviving insects.

TABLE 1

Effect of Snowdrop Lectin on larval development of *Spodoptera littoralis*

| Repli-cate | CONTROL | | SNOWDROP LECTIN | |
|---|---|---|---|---|
| | Initial Weight (g) | Final Weight (g)* | Initial Weight (g) | Final Weight(g)* |
| 1 | 0.15 | 0.17 | 0.13 | — |
| 2 | 0.2 | — | 0.14 | — |
| 3 | 0.02 | 0.35 | 0.21 | — |
| 4 | 0.2 | 0.25 | 0.17 | — |
| 5 | 0.14 | 0.18 | 0.15 | — |
| 6 | 0.22 | 0.36 | 0.14 | 0.14 |
| 7 | 0.12 | 0.16 | 0.10 | 0.12 |
| 8 | 0.17 | — | 0.10 | 0.17 |
| 9 | 0.17 | — | 0.12 | — |
| 10 | 0.2 | — | 0.18 | — |

*indicates larva died

EXAMPLE 3

Construction and transformation of Snowdrop lectin clones

The LECGNA2 clone contained a 570 base EcoRI linkered snowdrop lectin (GNA) gene cDNA cloned into the phagemid pT7T3 18U. The N-terminal and C-terminal peptides that are cleaved during processing to form the mature protein were marked on the sequence data.

The coding region of the lectin gene was subcloned into pUC19 using standard polymerase chain reaction [PCR] technology [Innis, M. A. et al. eds. PCR Protocols: A Guide to Methods and Applications. Academic Press, San Diego. 1990]. Oligonucleotide primers were made covering the N-terminal and C-terminal regions which incorporated restriction sites so that the resultant amplified fragments could be subcloned using a BamHI/KpnI double digest. These primers comprised the sequences:

N-terminus: 5'-CGGATCCATGGCTAAGGCAAGT SEQ ID NO: 4

C-terminus: 5'-CGGTACCTCATTACTTTGCCGT SEQ ID NO: 5

Fragments were amplified using PCR and the LECGNA2 DNA as a template. The amplified fragments were cloned into pUC19 which had been linearised with BamHI+KpnI. Recombinant plasmids were screened for the correct insert size with BamHI/KpnI. The resultant constructs were sequenced to ensure that no unwanted mutations had been created as artifacts of the PCR reaction.

Figure 3:
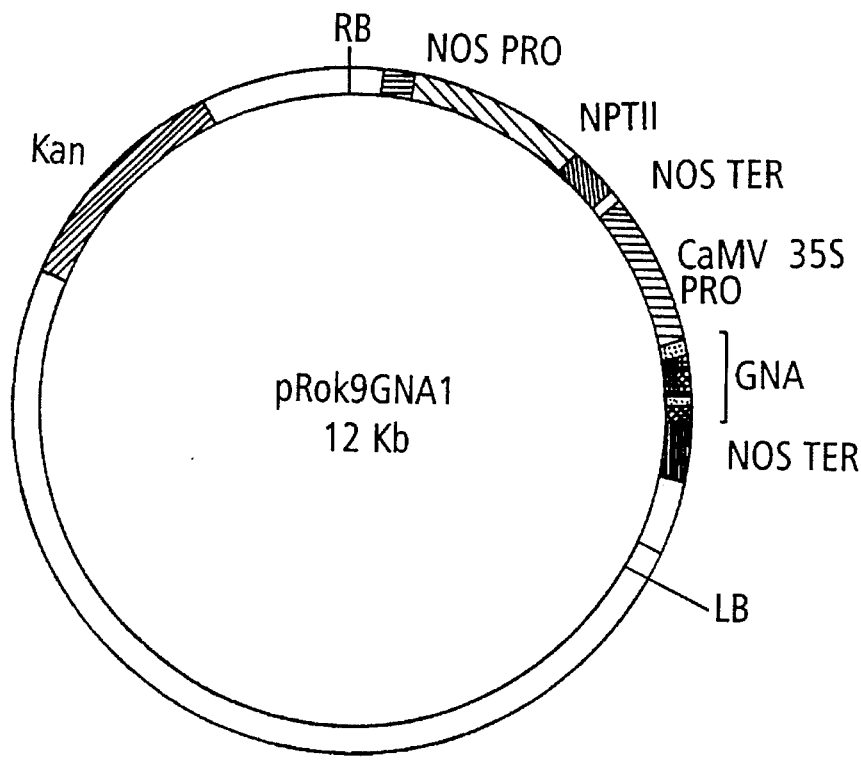
FIG. 3. Agrobacterium binary vector constructs useful for the constitutive expression of the snowdrop lectin gene in transgenic plants.

The GNA encoding fragment was isolated by digestion of the pUC19- 1GNA2 construct with BamHI/KpnI, ligated into BamHI/KpnI digested pROK2 and used to transform *E. coli* strain MC1022. These recombinants provided the Agrobacterium binary vector constructs which are useful for the constitutive expression of GNA in transgenic plants, illustrated in FIG. 3. Colonies were screened by restriction digestion using BamHI/KpnI, SphI and HindIII, and the correct pRok9GNA1 construct was mobilised into *Agrobacterium tumefaciens* strain LBA 4404 by triparental mating with pRK2013/HB101 according to established methods [Bevan, M. [1984] Binary Agrobacterium vectors for plant transformation. Nucleic Acids Research 12, 103–110]. Single colonies containing the pROK-GNA plasmids were rescreened by digestion with BamHI/KpnI to check for the correct insert size.

Transformation experiments were then carried out with *Nicotiana tabaccum* var Samsun using the standard leaf disc method [Horsch, R. B. et al. [1985] A simple and general method for transforming genes into plants. Science 227, 1229–1231]. Leaf discs were cultured on selective media containing kanamycin at 100 mg/l to select for transformed shoots. Shoots were rooted on kanamycin to eliminate untransformed escapes. Transformed plantlets were tested for snowdrop lectin expression by standard ELISA methods [Engvall, E. [1980] Meths. Enzymol. 70, 419]. Transgenic plants from lines 15GNA33, 15GNA35 and 15GNA79 express high levels of GNA antigen, equivalent to 40.2, 26.6 and 47.3 μg/g fresh weight respectively. The biological activity of the lectin in these plants may be demonstrated by standard haemagglutination assay procedures using trypsinised rabbit erythrocytes [Liss, H. & Sharon, N. [1973] The biochemistry of plant lectins [phaetohaemaggiutinins]. Ann. Rev. Biochem. 42, 541–574] on phosphate buffered saline extracts of free-dried leaf tissue.

EXAMPLE 4

Detached leaf bioassay v. *Heliothis virescens*

Clonally replicated transgenic plants from lines 15GNA33, 15GNA35 and 15GNA79 [produced as described in Example 3] were transferred to loam based compost [Levingtons M3; Fisons plc] in 5 inch pots and maintained in a growth room with a 12 h full, 4 h half light day regimen at 26° C., 65% RH.

Leaf samples [ca. 600 mm$^2$] were removed from transgenic plants and from control tobacco plants and placed in 3 oz plastic catering pots [DRG Plastics Ltd.] on top of two moistened filter paper discs. Samples were infested with 5 neonate [<24 h old] *H. virescens* larvae per replicate, sealed and maintained at 25° C. Live insects were removed to fresh leaf samples every 48 h. After 7 days all live insects were counted and weighed. All leaf samples were pressed and the leaf area eaten over the 7 days measured by image analysis. The results are summarised below:

Insect survival

G-test of association of number insects surviving with genotype.

| GENOTYPE | CORRECTED MORTALITY* | $G_{adj}$ | p [$H_0$:exp=con] |
|---|---|---|---|
| Control | 0 | — | — |
| 15GNA33 | 26 | 4.500 | <0.05 |
| 15GNA35 | 3 | 0.016 | N.S. |
| 15GNA79 | 16 | 0.710 | N.S. |
| Σ15GNA | 22 | 1.212 | N.S. |

*Corrected according to Abbott, W.S. [1925] A method of computing the effectiveness of an insecticide. J. Econ. Entomol. 18, 265–267.

Insect biomass per replicate

Non-parametric Mann-Whitney Utest. Data are presented as mean + S.E.M. but note that data was not normally distributed.

| GENOTYPE | N | BIOMASS | p [$H_0$: exp=con] |
|---|---|---|---|
| Control | 48 | 5.06 + 1.34 | — |
| 15GNA33 | 28 | 1.49 + 0.62 | <0.05 |
| 15GNA35 | 28 | 2.05 + 0.79 | N.S. |
| 15GNA79 | 28 | 0.75 + 0.24 | <0.01 |
| Σ15GNA | 84 | 1.43 + 0.35 | <0.01 |

Distributions of number insects per replicate

Figure 4:
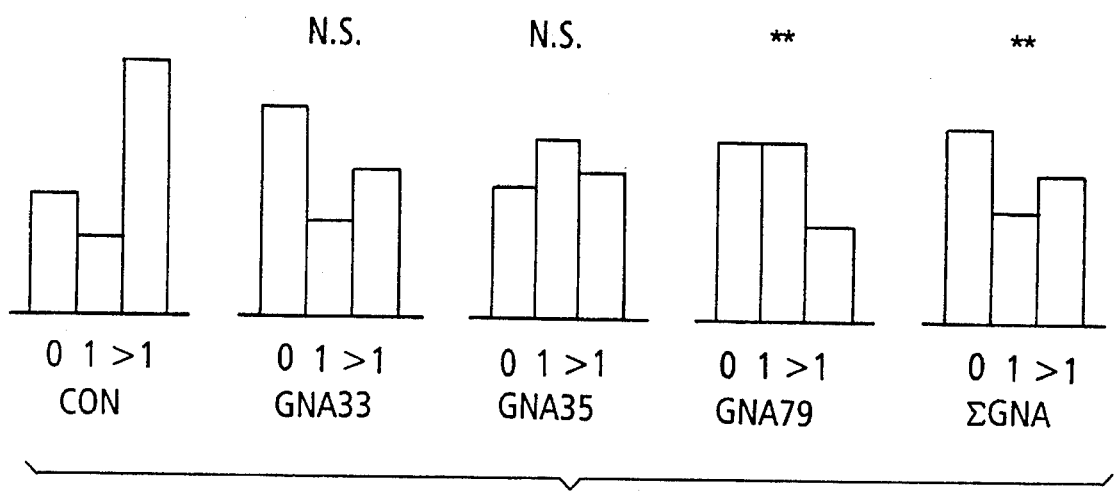
FIG. 4. Distributions of numbers of surviving *Heliothis virescens* larvae in detached leaf bioassays.

Classes simplified to 0, 1 or >1 insects per replicate. G-test [$H_0$:exp=con]. See FIG. 4.

Leaf area eaten per replicate

Mean leaf area eaten + S.E.M. in mm$^2$. Type I ANOVA.

| GENOTYPE | n | MEAN AREA | F | p [$H_0$: exp=con] |
|---|---|---|---|---|
| Control | 48 | 218 + 44 | — | — |
| 15GNA33 | 28 | 56 + 11 | 7.89 | <0.01 |
| 15GNA35 | 28 | 91 + 28 | 4.31 | <0.05 |
| 15GNA79 | 28 | 39 + 10 | 9.60 | <<0.01 |
| Σ15GNA | 84 | 62 + 11 | 19.01 | <<0.01 |

EXAMPLE 5

Anthers were removed from flowering transgenic plants of line 15GNA79 and used to fertilise emasculated untransformed control *N. tabacum* var. 'Samsun' plants. Resultant hybrid seed was sown in compost. Two leaf discs [5 mm diameter] were taken from seedlings at the 4 leaf stage and squashed between two sheets of nitrocellulose [BA85; Schleicher & Schuell]. Radioimmunoassay of the resultant 'squash blot' with rabbit anti-GNA primary antibody and 125I-donkey anti-rabbit IgG [Amersham International plc] secondary antibody using standard techniques [Jahn, R., Schiebler, W & Greengard, P. [1984] A quantitative dot-immunobinding assay for proteins using nitrocellulose membrane filters. Proc. natl. Acad. Sci. USA 81, 1684–1687] allowed the identification of GNA-expressing [GNA$^+$xCON] and non-expressing [GNA°xCON] segregants.

The resulting hybrid plants can be used for whole plant bioassays. Insect damage may be determined as described in Example 4.

| | |
|---|---|
| SEQUENCE ID NO: | LECGNA1 (equals SEQ ID NO: 6) |
| SEQUENCE TYPE: | Nucleotide sequence with corresponding protein |
| SEQUENCE LENGTH: | 610 bases |
| STRANDEDNESS: | Double-stranded |
| TOPLOGY: | Linear |
| MOLECULE TYPE: | cDNA to mRNA |
| ORIGINAL SOURCE ORGANISM: | *Galanthus nivalis* |
| EXPERIMENTAL SOURCE: | Clones |
| FEATURES: | from 1 to 67 bp putative signal peptide  P |
| | from 68 to 382 bp putative mature protein  P |
| | from 383 to 487 bp putative C-terminal peptide  P |
| | from 488 to 610 bp 3' untranslated region  P |

```
G GCT AAG ACA ATT CTC CTC ATT TTG GCC ACC ATC TTC CTT GGT GTC ATC      49
  Ala Lys Thr Ile Leu Leu Ile Leu Ala Thr Ile Phe Leu Gly Val Ile
          -20              -15                  -10

ACA CCA TCT TGC CTG AGT AAT AAT ATC CTG TAC TCT GGC GAG ACT CTC        97
Thr Pro Ser Cys Leu Ser Asn Asn Ile Leu Tyr Ser Gly Glu Thr Leu
    -5                   1               5                   10

TCT GCC GGC GAA TTT CTC AAC CAA GGC AAT TAT GTT TTT ATC ATG CAA        145
Ser Ala Gly Glu Phe Leu Asn Gln Gly Asn Tyr Val Phe Ile Met Gln
                15                  20                  25

GAG GAC TGC AAT CTG GTC TTG TAC GAC GTT GAC AAG CCT CTC TGG GAA        193
Glu Asp Cys Asn Leu Val Leu Tyr Asp Val Asp Lys Pro Leu Trp Glu
                30                  35                  40

ACA AAC ACA GGC GGC CTC TCC CGT CGC TGC TAT CTC AAC ATG CAG ACT        241
Thr Asn Thr Gly Gly Leu Ser Arg Arg Cys Tyr Leu Asn Met Gln Thr
            45                  50                  55

GAT GGG AAC CTC GTC GTG TAC AAC CCG TCG AAC AAA CCG ATT TGG GCA        289
Asp Gly Asn Leu Val Val Tyr Asn Pro Ser Asn Lys Pro Ile Trp Ala
        60                  65                  70

AGC AAC ACT GGA GGC CAG AAT GGT AAT TAT GTG TGC ATC CTT CAG AAG        337
Ser Asn Thr Gly Gly Gln Asn Gly Asn Tyr Val Cys Ile Leu Gln Lys
75                  80                  85                  90

GAT GGG AAC ATT GCG ATC TAC GGA CCT GCT ATT TGG GCT ACT GGA ACC        385
Asp Gly Asn Ile Ala Ile Tyr Gly Pro Ala Ile Trp Ala Thr Gly Thr
                95                  100                 105

AAT ATT CAT GGA GCT GGA ATA GTT GGA GTT CTT GGA TCA GCA CCA CAG        433
Asn Ile His Gly Ala Gly Ile Val Gly Val Leu Gly Ser Ala Pro Gln
            110                 115                 120

AAT TCT ACT GCT GAA ATG ATA AAG CTA GTG AGG AAG TAC CTA ATC ACT        481
Asn Ser Thr Ala Glu Met Ile Lys Leu Val Arg Lys Tyr Leu Ile Thr
        125                 130                 140

AAG TAA TTATGACCCG TGAGGTCCGG ACTGCATGTT TGTGAGAATG AGGAATAAAA         537
Lys

GTCCAACCAT GTGGTGGACT CCTGAAAATA AATAACTGCT ATGTATGATG TAATGGAGAC      597
TTATCTACTT TGC                                                         610
```

SEQUENCE ID NO: LECGNA2 (equals SEQ ID NO: 7)
SEQUENCE TYPE: Nucleotide sequence with corresponding protein
SEQUENCE LENGTH: 570 bases
STRANDEDNESS: Double-stranded
TOPOLOGY: Linear
MOLECULE TYPE: cDNA to mRNA
ORIGINAL SOURCE ORGANISM: *Galanthus nivalis*
EXPERIMENTAL SOURCE: Clones
FEATURES: from 1 to 17 bp 5' untranslated region    E
          from 18 to 86 bp signal peptide            E
          from 87 to 401 bp mature protein           E
          from 402 to 491 bp C-terminal peptide      E
          from 492 to 570 bp 3' untranslated region  E

```
CAACTACAAG TTACAAA ATG GCT AAG GCA AGT CTC CTC ATT TTG GCC GCC ATC     53
                   Met Ala Lys Ala SeR Leu Leu Ile Leu Ala Ala Ile
                               -20                      -15

TTC CTT GGT GTC ATC ACA CCA TCT TGC CTG AGT GAC AAT ATT TTG TAC        101
Phe Leu Gly Val Ile Thr Pro Ser Cys Leu Ser Asp Asn Ile Leu Tyr 5
    -10                 -5                  1

TCC GGT GAG ACT CTC TCT ACA GGG GAA TTT CTC AAC TAC GGA AGT TTC        149
Ser Gly Glu Thr Leu Ser Thr Gly Glu Phe Leu Asn Tyr Gly Ser Phe
                10                  15                  20

GTT TTT ATC ATG CAA GAG GAC TGC AAT CTG GTC TTG TAC GAC GTG GAC        197
Val Phe Ile Met Gln Glu Asp Cys Asn Leu Val Leu Tyr Asp Val Asp
            25                  30                  35

AAG CCA ATC TGG GCA ACA AAC ACA GGT GGT CTC TCC CGT AGC TGC TTC        245
Lys Pro Ile Trp Ala Thr Asn Thr Gly Gly Leu Ser Arg Ser Cys Phe
        40                  45                  50

CTC AGC ATG CAG ACT GAT GGG AAC CTC GTG GTG TAC AAC CCA TCG AAC        293
Leu Ser Met Gln Thr Asp Gly Asn Leu Val Val Tyr Asn Pro Ser Asn
    55                  60                  65
```

```
AAA CCG ATT TGG GCA AGC AAC ACT GGA GGC CAA AAT GGG AAT TAC GTG       341
Lys Pro Ile Trp Ala Ser Asn Thr Gly Gly Gln Asn Gly Asn Tyr Val
 70              75                  80                  85

TGC ATC CTA CAG AAG GAT AGG AAT GTT GTG ATC TAC GGA ACT GAT CGT       389
Cys Ile Leu Gln Lys Asp Arg Asn Val Val Ile Tyr Gly Thr Asp Arg
             90                  95                 100

TGG GCT ACT GGA ACT CAC ACC GGA CTT GTT GGA ATT CCC GCA TCG CCA       437
Trp Ala Thr Gly Thr His Thr Gly Leu Val Gly Ile Pro Ala Ser Pro
            105                 110                 115

CCC TCA GAG AAA TAT CCT ACT GCT GGA AAG ATA AAG CTT GTG ACG GCA       485
Pro Ser Glu Lys Tyr Pro Thr Ala Gly Lys Ile Lys Leu Val Thr Ala
            120                 125                 130

AAG TAA TGACCGGTGA TCTTTTAACT TGCATGTATG TGGGAASGAGT AATAAAATAA       541
Lys

GTGCATTTGA GATAATCGAC CTCGTCGCG                                       570
```

SEQUENCE ID NO: LECGNA3 (equals SEQ ID NO: 8)
SEQUENCE TYPE: Nucleotide sequence with corresponding protein
SEQUENCE LENGTH: 667 bases
STRANDEDNESS: Double-stranded
TOPOLOGY: Linear
MOLECULE TYPE: cDNA to mRNA
ORIGINAL SOURCE ORGANISM: *Galanthus nivalis*
EXPERIMENTAL SOURCE: Clones
FEATURES: from 1 to 62 bp putative signal peptide          P
from 63 to 377 bp putative mature protein                   P
from 378 to 467 bp putative C-terminal peptide              P
from 468 to 667 bp 3' untranslated region                   P

```
AG ACA ATT CTC CTC ATT TTG GCC ACC ATC TTC CTT GGA GTC ATC ACA CCA     50
   Thr Ile Leu Leu Ile Leu Ala Thr Ile Phe Leu Gly Val Ile Thr Pro
                      -15                 -10                 -5

TCT TGC CTG AGT GAA AAT GTT CTG TAC TCC GGT GAG ACT CTC CCT ACA        98
Ser Cys Leu Ser Glu Asn Val Leu Tyr Ser Gly Glu Thr Leu Pro Thr
              1                   5

GGG GGA TTT CTC TCC TCT GGC AGT TTT GTT TTT ATC ATG CAA GAG GAC       146
Gly Gly Phe Leu Ser Ser Gly Ser Phe Val Phe Ile Met Gln Glu Asp
             15                  20                  25

TGC AAC CTG GTC CTG TAC AAC GTC GAC AAG CCC ATC TGG GCA ACT AAC       194
Cys Asn Leu Val Leu Tyr Asn Val Asp Lys Pro Ile Trp Ala Thr Asn
         30                  35                  40

ACA GGC GGC CTC TCC AGT GAC TGC ACC CTC AGC ATG CAG ACC GAT GGG       242
Thr Gly Gly Leu Ser Ser Asp Cys Thr Leu Ser Met Gln Thr Asp Gly
 45              50                  55                      60

AAC CTC GTA GTG TAC ACC CCA TCG AAC AAA CCG ATT TGG GCA AGC AAC       290
Asn Leu Val Val Tyr Thr Pro Ser Asn Lys Pro Ile Trp Ala Ser Asn
                 65                  70                  75

ACT GAC AGC CAG AAT GGG CAT TAC GTG TGC ATC CTT CAA AAG GAT CGG       338
Thr Asp Ser Gln Asn Gly His Tyr Val Cys Ile Leu Gln Lys Asp Arg
             80                  85                  90

AAC GTT GTG ATC TAC GGA ACT GAT CGT TGG GCT ACA GGA ACT TAC ACC       386
Asn Val Val Ile Tyr Gly Thr Asp Arg Trp Ala Thr Gly Thr Tyr Thr
             95                 100                 105

GGT GCT GTT GGA ATT CCT GAA TCA CCC CCC TCG GAG AAA TAT CCT ACT       434
Gly Ala Val Gly Ile Pro Glu Ser Pro Pro Ser Glu Lys Tyr Pro Thr
        110                 115                 120

GCT GGA AAG ATA AAG CAA GTG ACC GAA AAG TAA TGACCGGTGA TCTATGAACC     487
Ala Gly Lys Ile Lys Gln Val Thr Glu Lys
130                 135

TTGCATGCAT GTGAGAAGAG TAATATAATA TATGTGCATT TTAGATCAAT GCACACGGTG     547
TTTCTTTGTC ACAAATAAAT AACTAGGTTG TACTGGACGT AAATAAAGTC CGGCCTCCTA     607
GTTTCGTGCC TTGTACGCA TCTTGTATGC ATGCATTTTG GAAAGGAGGC                 667
```

SEQUENCE ID NO: LECGNA5 (equals SEQ ID NO: 9)
SEQUENCE TYPE: Nucleotide sequence with corresponding protein
SEQUENCE LENGTH: 650 bases
STRANDENDESS: Double-stranded -continued

```
              TOPOLOGY: Linear
         MOLECULE TYPE: cDNA to mRNA
ORIGINAL SOURCE ORGANISM: Galanthus nivalis
   EXPERIMENTAL SOURCE: Clones
              FEATURES: from 1 to 63 bp putative signal peptide           P
                        from 64 to 378 bp putative mature protein         P
                        from 379 to 468 bp putative C-terminal peptide    P
                        from 469 to 650 bp 3' untranslated region         P
```

```
AAG ACA AGT CTC CTC ATT TTG GCC ACC ATC TTC CTT GGA GTC ATC GCA    48
Lys Thr Ser Leu Leu Ile Leu Ala Thr Ile Phe Leu Gly Val Ile Ala
    -20              -15              -10

CCA TCT TGC CTG AGT GAA AAT ATT CTG TAC TCC GGT GAG ACT CTC CCT    96
Pro Ser Cys Leu Ser Glu Asn Ile Leu Tyr Ser Gly Glu Thr Leu Pro
 -5               1                5                    10

ACA GGG GGA TTT CTC TCC TCT GGC AGT TTT GTT TTT ATC ATG CAA GAG   144
Thr Gly Gly Phe Leu Ser Ser Gly Ser Phe Val Phe Ile Met Gln Glu
            15              20                  25

GAC TGC AAC CTG GTC TTG TAC AAC GTC GAC AAG CCC ATC TGG GCA ACT   192
Asp Cys Asn Leu Val Leu Tyr Asn Val Asp Lys Pro Ile Trp Ala Thr
                        35                  40

AAC ACT GGT GGC CTC TCC AGT GAC TGC TCC CTC AGC ATG CAG ACA GAT   240
Asn Thr Gly Gly Leu Ser Ser Asp Cys Ser Leu Ser Met Gln Thr Asp
        45              50                  55

GGG AAC CTC GTA GTG TAC ACC CCA TCG AAC AAA CCG ATT TGG GCA AGC   288
Gly Asn Leu Val Val Tyr Thr Pro Ser Asn Lys Pro Ile Trp Ala Ser
 60              65                  70                      75

AAC ACT GAC GGC CAG AAT GGG AAT TAC GTG TGC ATC CTT CAA AAG GAT   336
Asn Thr Asp Gly Gln Asn Gly Asn Tyr Val Cys Ile Leu Gln Lys Asp
                    80                  85                  90

CGG AAC GTT GTG ATC TAC GGA ACT AAT CGT TGG GCT ACT GGA ACT CAC   384
Arg Asn Val Val Ile Tyr Gly Thr Asn Arg Trp Ala Thr Gly Thr His
                95                  100                 105

ACC GGT GCT GTA GGA ATT CCT GCA TCA CCG CCC TCG GAG AAA TAT CCT   432
Thr Gly Ala Val Gly Ile Pro Ala Ser Pro Pro Ser Glu Lys Tyr Pro
            110                 115                 120

ACT GCT GGA ATG ATA AAG CAA GTG ACC GAA AAG TAA TGACCGGTGG        478
Thr Ala Gly Met Ile Lys Gln Val Thr Glu Lys

TGATCTATGA ACCTTGCATG CATGTGAGAA GAGTAATAAA ATATGTGCAT TTTAGATCAA   538
TGCACACGGT GTTTGTTTGT CACAAATAAA TAACTAGGTT GTACTGGACA TAAATATAGT   598
CCCGCCTCCT GGTTTCATGC CTTGTACGCA TCTTCTATGC ATGCATTTTG GA          650
```

```
     SEQUENCE ID NO: LECGNA8 (equals SEQ ID NO: 10)
       SEQUENCE TYPE: Nucleotide sequence with corresponding protein
     SEQUENCE LENGTH: 597 bases
        STRANDEDNESS: Double-stranded
            TOPOLOGY: Linear
       MOLECULE TYPE: cDNA to mRNA
ORIGINAL SOURCE ORGANISM: Galanthus nivalis
 EXPERIMENTAL SOURCE: Clones
            FEATURES: from 1 to 61 bp putative signal peptide           P
                      from 62 to 376 bp putative mautre protein         P
                      from 377 to 481 bp putative C-terminal peptide    P
                      from 482 to 597 bp 3' untranslated region         P
```

```
G ACA AGT CTC CTC ATT TTG GCC ACC ATC TTC CTT GGA GTC ATC ACA CCA    49
  Thr Ser Leu Leu Ile Leu Ala Thr Ile Phe Leu Gly Val Ile Thr Pro
      -20              -15              -10                      -5

TCT TGC CTG AGT GAT AAT ATT ATG TAC TCT GGC GAG ACT CTC TCT ACT     97
Ser Cys Leu Ser Asp Asn Ile Met Tyr Ser Gly Glu Thr Leu Ser Thr
             1                5                    10

GGC GAA TTT CTC AAC TAC GGC AGT TAT GTT TTT ATC ATG CAA GAG GAC   145
Gly Glu Phe Leu Asn Tyr Gly Ser Tyr Val Phe Ile Met Gln Glu Asp
         15              20                  25

TGC AAT CTG GTC TTG TAC GAC GTT GAC AAG CCT ATC TGG GCA ACA AAC   193
Cys Asn Leu Val Leu Tyr Asp Val Asp Lys Pro Ile Trp Ala Thr Asn
     30              35                  40
```

-continued

| | | | | | | | | | | | | | | | | |
|---|---|---|---|---|---|---|---|---|---|---|---|---|---|---|---|---|
| ACA | GGT | GGC | CTC | TCC | CGT | AGC | TGC | TAT | CTC | AAC | ATG | CAG | ACC | GAC | GGG | 241 |
| Thr | Gly | Gly | Leu | Ser | Arg | Ser | Cys | Tyr | Leu | Asn | Met | Gln | Thr | Asp | Gly | |
| 45 | | | | | 50 | | | | | 55 | | | | | 60 | |
| AAC | CTC | GTC | GTG | TAC | AAC | CCG | TCG | AAC | AAA | CCG | ATT | TGG | GCA | AGC | AAC | 289 |
| Asn | Leu | Val | Val | Tyr | Asn | Pro | Ser | Asn | Lys | Pro | Ile | Trp | Ala | Ser | Asn | |
| | | | | 65 | | | | | 70 | | | | | 75 | | |
| ACT | GGA | GGC | CAG | AAT | GGT | AAT | TAT | GTG | TGC | ATC | CTT | CAG | AAG | GAT | CGG | 337 |
| Thr | Gly | Gly | Gln | Asn | GLy | Asn | Tyr | Val | Cys | Ile | Leu | Gln | Lys | Asp | Arg | |
| | | | 80 | | | | | 85 | | | | | 90 | | | |
| AAC | GTT | GTG | ATC | TAC | GGA | CCT | GCT | CGT | TGG | GCT | ACT | GGA | ACC | AAT | ATT | 385 |
| Asn | Val | Val | Ile | Tyr | Gly | Pro | Ala | Arg | Trp | Ala | Thr | Gly | Thr | Asn | Ile | |
| | | | 95 | | | | 100 | | | | | 105 | | | | |
| CAT | GGT | GCT | GGA | ATA | GTT | GGA | GTT | CCT | GGA | TCA | GCA | CCA | CAG | AAT | TCT | 433 |
| His | Gly | Ala | Gly | Ile | Val | Gly | Val | Pro | Gly | Ser | Ala | Pro | Gln | Asn | Ser | |
| | | 110 | | | | 115 | | | | | 120 | | | | | |
| ACT | GCT | GAA | ATG | ATA | AAG | CTA | GTG | AGG | AAG | TAC | CTA | ATC | ACT | AAG | TAA | 481 |
| Thr | Ala | Glu | Met | Ile | Lys | Leu | Val | Arg | Lys | Tyr | Leu | Ile | Thr | Lys | | |
| 125 | | | | | 130 | | | | | 135 | | | | | | |

TTATGACCCG TGAGGTCCGG GCTGCATGTG TGTGAGAATG AGGAATAAAA GTAAAACCAT 541
GTGGTGGACG TGCTGAAAAT AAATAACTGC TATGTATGAT GTAATGGAGA CTTATC 597

---

We claim:

1. A method of controlling insect pests, which comprises applying to the insect pests or their environment a lectin having specific mannose-binding ability and derived from Amaryllidaceae or Alliaceae.

2. A method according to claim 1, in which the lectin is applied to plants in order to protect the plants against insect pests.

3. A method according to claim 2, in which the lectin is applied by treating the plants with a composition comprising the lectin.

4. A method according to claim 2, in which the lectin is applied by genetically transforming the plants so that the plants and their progeny express the lectin which does not occur naturally in them.

5. A method according to claim 1, in which the lectin has a sequence identical to the protein of Sequence ID Nos. 6 to 10.

6. A method according to any one of claims 1 to 4, in which the insect pests are of the Coleoptera order.

7. A transgenic plant containing and capable of expressing a gene coding for a lectin having specific mannose-binding ability and derived from Amaryllidaceae or Alliaceae, or the progeny of such a plant.

8. A transgenic plant according to claim 7, in which the lectin has a sequence identical to the protein of Sequence ID Nos. 6 to 10.

9. An isolated recombinant DNA molecule comprising a gene for a lectin having specific mannose-binding ability and from plants in the families Amaryllidaceae or Alliaceae.

10. An isolated recombinant DNA molecule according to claim 9, having a sequence identical to the protein of Sequence ID Nos. 6 to 10.

11. A recombinant DNA plasmid within which is incorporated a DNA molecule according to claim 9 or 10.

12. A method of making a transgenic plant according to claim 7 or 8, which comprises incorporating a DNA molecule according to claim 9 or 10 into the nuclear genome of said plant and obtaining expression of lectins having specific mannose-binding ability and derived from Amaryllidaceae or Alliaceae.

13. A transgenic plant produced by the method of claim 12, or the progeny of such a plant.

14. An isolated recombinant lectin having a sequence substantially the same as the protein of Sequence ID Nos. 6 to 10, or a subunit thereof having specific mannose-binding ability.

15. A method according to claim 5 in which the insect pests are of the Coleoptera order.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TGTGTTTGTT GCCCA    15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TGTGTTTGTA GCCCA    15

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

TGTGTTTGTG GCCCA                                                                                              15

(2) INFORMATION FOR SEQ ID NO:4:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

CGGATCCATG GCTAAGGCAA GT                                                                                      22

(2) INFORMATION FOR SEQ ID NO:5:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CGGTACCTCA TTACTTTGCC GT                                                                                      22

(2) INFORMATION FOR SEQ ID NO:6:

(i) SEQUENCE CHARACTERISTICS:
    (A) LENGTH: 610 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (A) ORGANISM: Galantus nivalis (ix) FEATURE:
    (A) NAME/KEY: misc_feature
    (B) LOCATION: 1..67
    (D) OTHER INFORMATION: /note="Putative signal peptide"

(ix) FEATURE:
    (A) NAME/KEY: misc_feature
    (B) LOCATION: 68..382
    (D) OTHER INFORMATION: /note="Putative mature protein"

(ix) FEATURE:
    (A) NAME/KEY: misc_feature (B) LOCATION: 383..487
(D) OTHER INFORMATION: /note="Putative C-terminal peptide"

(ix) FEATURE:
(A) NAME/KEY: misc_feature
(B) LOCATION: 488..610
(D) OTHER INFORMATION: /note="3'untranslated region"

(xi) SEQUENCE DESCRIPTION: SEQ ID NO:6:

| | | | | | | |
|---|---|---|---|---|---|---|
| GGCTAAGACA | ATTCTCCTCA | TTTTGGCCAC | CATCTTCCTT | GGTGTCATCA | CACCATCTTG | 60 |
| CCTGAGTAAT | AATATCCTGT | ACTCTGGCGA | GACTCTCTCT | GCCGGCGAAT | TTCTCAACCA | 120 |
| AGGCAATTAT | GTTTTTATCA | TGCAAGAGGA | CTGCAATCTG | GTCTTGTACG | ACGTTGACAA | 180 |
| GCCTCTCTGG | GAAACAAACA | CAGGCGGCCT | CTCCCGTCGC | TGCTATCTCA | ACATGCAGAC | 240 |
| TGATGGGAAC | CTCGTCGTGT | ACAACCCGTC | GAACAAACCG | ATTTGGGCAA | GCAACACTGG | 300 |
| AGGCCAGAAT | GGTAATTATG | TGTGCATCCT | TCAGAAGGAT | GGGAACATTG | CGATCTACGG | 360 |
| ACCTGCTATT | TGGGCTACTG | GAACCAATAT | TCATGGAGCT | GGAATAGTTG | GAGTTCTTGG | 420 |
| ATCAGCACCA | CAGAATTCTA | CTGCTGAAAT | GATAAAGCTA | GTGAGGAAGT | ACCTAATCAC | 480 |
| TAAGTAATTA | TGACCCGTGA | GGTCCGGACT | GCATGTTTGT | GAGAATGAGG | AATAAAAGTC | 540 |
| CAACCATGTG | GTGGACTCCT | GAAAATAAAT | AACTGCTATG | TATGATGTAA | TGGAGACTTA | 600 |
| TCTACTTTGC | | | | | | 610 |

(2) INFORMATION FOR SEQ ID NO:7:

(i) SEQUENCE CHARACTERISTICS:
(A) LENGTH: 570 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Galanthus nivalis (ix) FEATURE:
(A) NAME/KEY: misc_feature
(B) LOCATION: 1..17
(D) OTHER INFORMATION: /note="5'untranslated region"

(ix) FEATURE:
(A) NAME/KEY: misc_feature
(B) LOCATION: 18..86
(D) OTHER INFORMATION: /note="Signal peptide"

(ix) FEATURE:
(A) NAME/KEY: misc_feature
(B) LOCATION: 87..401
(D) OTHER INFORMATION: /note="Mature protein"

(ix) FEATURE:
(A) NAME/KEY: misc_feature
(B) LOCATION: 402..491
(D) OTHER INFORMATION: /note="C-terminal peptide"

(ix) FEATURE:
(A) NAME/KEY: misc_feature
(B) LOCATION: 492..570
(D) OTHER INFORMATION: /note="3'untranslated region"

(xi) SEQUENCE DESCRIPTION: SEQ ID NO:7:

| | | | | | | |
|---|---|---|---|---|---|---|
| CAACTACAAG | TTACAAAATG | GCTAAGGCAA | GTCTCCTCAT | TTTGGCCGCC | ATCTTCCTTG | 60 |

```
GTGTCATCAC ACCATCTTGC CTGAGTGACA ATATTTTGTA CTCCGGTGAG ACTCTCTCTA    120

CAGGGGAATT TCTCAACTAC GGAAGTTTCG TTTTTATCAT GCAAGAGGAC TGCAATCTGG    180

TCTTGTACGA CGTGGACAAG CCAATCTGGG CAACAAACAC AGGTGGTCTC TCCCGTAGCT    240

GCTTCCTCAG CATGCAGACT GATGGGAACC TCGTGGTGTA CAACCCATCG AACAAACCGA    300

TTTGGGCAAG CAACACTGGA GGCCAAAATG GAATTACGT GTGCATCCTA CAGAAGGATA    360

GGAATGTTGT GATCTACGGA ACTGATCGTT GGGCTACTGG AACTCACACC GGACTTGTTG    420

GAATTCCCGC ATCGCCACCC TCAGAGAAAT ATCCTACTGC TGGAAAGATA AAGCTTGTGA    480

CGGCAAAGTA ATGACCGGTG ATCTTTTAAC TTGCATGTAT GTGGGAAGAG TAATAAAATA    540

AGTGCATTTG AGATAATCGA CCTCGTCGCG                                     570
```

( 2 ) INFORMATION FOR SEQ ID NO:8:

( i ) SEQUENCE CHARACTERISTICS:
( A ) LENGTH: 667 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: Galanthus nivalis ( i x ) FEATURE:
( A ) NAME/KEY: misc_feature
( B ) LOCATION: 1..62
( D ) OTHER INFORMATION: /note="Putative signal peptide"

( i x ) FEATURE:
( A ) NAME/KEY: misc_feature
( B ) LOCATION: 63..377
( D ) OTHER INFORMATION: /note="Putative mature protein"

( i x ) FEATURE:
( A ) NAME/KEY: misc_feature
( B ) LOCATION: 378..467
( D ) OTHER INFORMATION: /note="Putative C-terminal peptide"

( i x ) FEATURE:
( A ) NAME/KEY: misc_feature
( B ) LOCATION: 468..667
( D ) OTHER INFORMATION: /note="3'untranslated region"

( x i ) SEQUENCE DESCRIPTION: SEQ ID NO:8:

```
AGACAATTCT CCTCATTTTG GCCACCATCT TCCTTGGAGT CATCACACCA TCTTGCCTGA     60

GTGAAAATGT TCTGTACTCC GGTGAGACTC TCCCTACAGG GGGATTTCTC TCCTCTGGCA    120

GTTTTGTTTT TATCATGCAA GAGGACTGCA ACCTGGTCCT GTACAACGTC GACAAGCCCA    180

TCTGGGCAAC TAACACAGGC GGCCTCTCCA GTGACTGCAC CCTCAGCATG CAGACCGATG    240

GGAACCTCGT AGTGTACACC CCATCGAACA AACCGATTTG GCAAGCAAC ACTGACAGCC     300

AGAATGGGCA TTACGTGTGC ATCCTTCAAA GGATCGGAA CGTTGTGATC TACGGAACTG     360

ATCGTTGGGC TACAGGAACT TACACCGGTG CTGTTGGAAT TCCTGAATCA CCCCCCTCGG    420

AGAAATATCC TACTGCTGGA AAGATAAAGC AAGTGACCGA AAAGTAATGA CCGGTGATCT    480

ATGAACCTTG CATGCATGTG AGAAGAGTAA TATAATATAT GTGCATTTTA GATCAATGCA    540

CACGGTGTTT CTTTGTCACA AATAAATAAC TAGGTTGTAC TGGACGTAAA TAAAGTCCGG    600

CCTCCTAGTT TCGTGCCTTG TACGCATCTT GTACGCATCT TGTATGCATG CATTTTGGAA    660
```

AGGAGGC                                                                                      667

( 2 ) INFORMATION FOR SEQ ID NO:9:

( i ) SEQUENCE CHARACTERISTICS:
        ( A ) LENGTH: 650 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Galanthus nivalis ( i x ) FEATURE:
        ( A ) NAME/KEY: misc_feature
        ( B ) LOCATION: 1..63
        ( D ) OTHER INFORMATION: /note="Putative signal peptide"

( i x ) FEATURE:
        ( A ) NAME/KEY: misc_feature
        ( B ) LOCATION: 64..378
        ( D ) OTHER INFORMATION: /note="Putative mature protein"

( i x ) FEATURE:
        ( A ) NAME/KEY: misc_feature
        ( B ) LOCATION: 379..468
        ( D ) OTHER INFORMATION: /note="Putative C-terminal
              peptide"

( i x ) FEATURE:
        ( A ) NAME/KEY: misc_feature
        ( B ) LOCATION: 469..650
        ( D ) OTHER INFORMATION: /note="3'untranslated region"

( x i ) SEQUENCE DESCRIPTION: SEQ ID NO:9:

| | | | | | |
|---|---|---|---|---|---|
| AAGACAAGTC | TCCTCATTTT | GGCCACCATC | TTCCTTGGAG | TCATCGCACC | ATCTTGCCTG | 60 |
| AGTGAAAATA | TTCTGTACTC | CGGTGAGACT | CTCCCTACAG | GGGGATTTCT | CTCCTCTGGC | 120 |
| AGTTTTGTTT | TTATCATGCA | AGAGGACTGC | AACCTGGTCT | TGTACAACGT | CGACAAGCCC | 180 |
| ATCTGGGCAA | CTAACACTGG | TGGCCTCTCC | AGTGACTGCT | CCCTCAGCAT | GCAGACAGAT | 240 |
| GGGAACCTCG | TAGTGTACAC | CCCATCGAAC | AAACCGATTT | GGGCAAGCAA | CACTGACGGC | 300 |
| CAGAATGGGA | ATTACGTGTG | CATCCTTCAA | AAGGATCGGA | ACGTTGTGAT | CTACGGAACT | 360 |
| AATCGTTGGG | CTACTGGAAC | TCACACCGGT | GCTGTAGGAA | TTCCTGCATC | ACCGCCCTCG | 420 |
| GAGAAATATC | CTACTGCTGG | AATGATAAAG | CAAGTGACCG | AAAAGTAATG | ACCGGTGGTG | 480 |
| ATCTATGAAC | CTTGCATGCA | TGTGAGAAGA | GTAATAAAAT | ATGTGCATTT | TAGATCAATG | 540 |
| CACACGGTGT | TTGTTTGTCA | CAAATAAATA | ACTAGGTTGT | ACTGGACATA | AATATAGTCC | 600 |
| CGCCTCCTGG | TTTCATGCCT | TGTACGCATC | TTCTATGCAT | GCATTTTGGA | | 650 |

( 2 ) INFORMATION FOR SEQ ID NO:10:

( i ) SEQUENCE CHARACTERISTICS:
        ( A ) LENGTH: 597 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
 ( A ) ORGANISM: Galanthus nivalis ( i x ) FEATURE:
 ( A ) NAME/KEY: misc_feature
 ( B ) LOCATION: 1..61
 ( D ) OTHER INFORMATION: /note="Putative signal peptide"

( i x ) FEATURE:
 ( A ) NAME/KEY: misc_feature
 ( B ) LOCATION: 62..376
 ( D ) OTHER INFORMATION: /note="Putative mature protein"

( i x ) FEATURE:
 ( A ) NAME/KEY: misc_feature
 ( B ) LOCATION: 377..481
 ( D ) OTHER INFORMATION: /note="Putative C-terminal peptide"

( i x ) FEATURE:
 ( A ) NAME/KEY: misc_feature
 ( B ) LOCATION: 482..597
 ( D ) OTHER INFORMATION: /note="3'untranslated region"

( x i ) SEQUENCE DESCRIPTION: SEQ ID NO:10:

| | | | | | | |
|---|---|---|---|---|---|---|
| GACAAGTCTC | CTCATTTTGG | CCACCATCTT | CCTTGGAGTC | ATCACACCAT | CTTGCCTGAG | 60 |
| TGATAATATT | ATGTACTCTG | GCGAGACTCT | CTCTACTGGC | GAATTTCTCA | ACTACGGCAG | 120 |
| TTATGTTTTT | ATCATGCAAG | AGGACTGCAA | TCTGGTCTTG | TACGACGTTG | ACAAGCCTAT | 180 |
| CTGGGCAACA | AACACAGGTG | GCCTCTCCCG | TAGCTGCTAT | CTCAACATGC | AGACCGACGG | 240 |
| GAACCTCGTC | GTGTACAACC | CGTCGAACAA | ACCGATTTGG | GCAAGCAACA | CTGGAGGCCA | 300 |
| GAATGGTAAT | TATGTGTGCA | TCCTTCAGAA | GGATCGGAAC | GTTGTGATCT | ACGGACCTGC | 360 |
| TCGTTGGGCT | ACTGGAACCA | ATATTCATGG | TGCTGGAATA | GTTGGAGTTC | CTGGATCAGC | 420 |
| ACCACAGAAT | TCTACTGCTG | AAATGATAAA | GCTAGTGAGG | AAGTACCTAA | TCACTAAGTA | 480 |
| ATTATGACCC | GTGAGGTCCG | GGCTGCATGT | GTGTGAGAAT | GAGGAATAAA | AGTAAAACCA | 540 |
| TGTGGTGGAC | GTGCTGAAAA | TAAATAACTG | CTATGTATGA | TGTAATGGAG | ACTTATC | 597 |